United States Patent
Wilkinson

(10) Patent No.: US 7,041,066 B2
(45) Date of Patent: May 9, 2006

(54) NEEDLE ASSEMBLY

(75) Inventor: Bradley M. Wilkinson, North Haledon, NJ (US)

(73) Assignee: Becton, Dickinson & Company, Franklin Lakes, NJ (US)

(*) Notice: Subject to any disclaimer, the term of this patent is extended or adjusted under 35 U.S.C. 154(b) by 406 days.

(21) Appl. No.: 10/387,919

(22) Filed: Mar. 13, 2003

(65) Prior Publication Data

US 2004/0181173 A1 Sep. 16, 2004

(51) Int. Cl.
*A61B 5/00* (2006.01)
*B65D 81/00* (2006.01)

(52) U.S. Cl. .................................... 600/576
(58) Field of Classification Search ............. 600/576; 604/110, 263, 198; 128/899
See application file for complete search history.

(56) References Cited

U.S. PATENT DOCUMENTS

| | | | |
|---|---|---|---|
| 5,176,655 A | 1/1993 | McCormick et al. | |
| 5,246,427 A | 9/1993 | Sturman et al. | |
| 5,423,766 A | 6/1995 | Di Cesare | |
| 5,429,611 A | 7/1995 | Rait | |
| 5,584,818 A | 12/1996 | Morrison | |
| 5,919,168 A | 7/1999 | Wheeler | |
| 5,951,525 A | 9/1999 | Thorne et al. | |
| 5,957,892 A | 9/1999 | Thorne | |
| 6,004,294 A | 12/1999 | Brimhall et al. | |
| RE36,885 E | 9/2000 | Blecher et al. | |
| D452,314 S | 12/2001 | Niermann | |
| 6,443,929 B1 | 9/2002 | Kuracina et al. | |
| 6,537,259 B1* | 3/2003 | Niermann | 604/263 |
| 6,682,510 B1* | 1/2004 | Niermann | 604/263 |
| 6,855,130 B1* | 2/2005 | Saulenas et al. | 604/110 |
| 2002/0004650 A1 | 1/2002 | Kuracina et al. | |
| 2002/0065488 A1 | 5/2002 | Yousuke et al. | |
| 2002/0103465 A1* | 8/2002 | Crowford et al. | 604/263 |

FOREIGN PATENT DOCUMENTS

| | | |
|---|---|---|
| EP | 1132103 A | 9/2001 |
| EP | 1221305 A | 7/2002 |
| EP | 1350538 A | 10/2003 |

\* cited by examiner

Primary Examiner—Max F. Hindenburg
Assistant Examiner—Brian Szmal
(74) *Attorney, Agent, or Firm*—Mark Lindsey; Hoffman & Baron LLP

(57) ABSTRACT

A needle shield assembly includes an elongate needle having a proximal end and a distal needle tip. A needle shield is provided for slidable movement from a retracted position in which the needle tip is exposed to an extended position in which the needle tip is covered. A flexible actuator is fixedly positioned toward the proximal end of the needle and releasably connected to the needle shield for actuatable release thereof. A resilient band attached to the shield urges the shield along the needle to cover the distal tip upon release of the connection between the shield and the actuator.

39 Claims, 20 Drawing Sheets

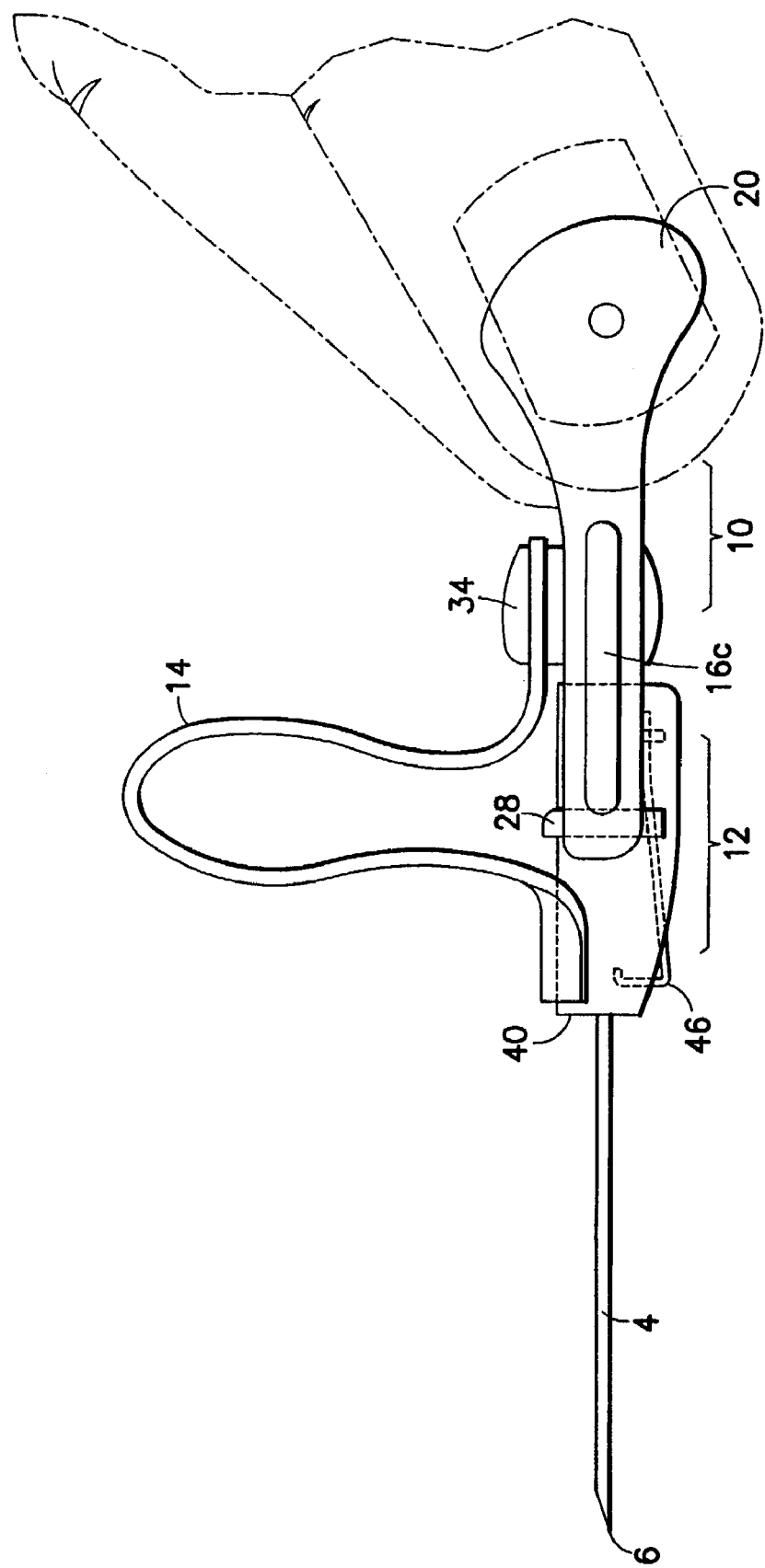

NEEDLE ASSEMBLY

BACKGROUND OF THE INVENTION

1. Field of the Invention

The present invention relates generally to needle shield assemblies for blood collection/intravenous infusion devices. More particularly, the present invention relates to a needle assembly having a needle shield that may be activated by a single-handed operation in order to avoid accidental needle sticks.

2. Description of the Prior Art

A conventional IV infusion or blood collection assembly includes elongated small gauge plastic flexible tubing material having a disposable needle and a body or hub for holding the needle on one end. Usually, the hub is adhered to one end of the flexible tube by a friction fit. The hub includes wings extending on either side for the phlebotomist or user to grasp and position the hub for inserting the needle into a patient. Such assemblies may be used for infusing medication into a patient or for collecting blood from a patient. Generally, at the end of the flexible tube opposite the needle is a female connection for connecting supplies of fluid to be infused or for connecting apparatus for collecting blood, as required.

After the needle of the assembly has been withdrawn from a patient, protection of the used needle tip becomes important. Accidental sticks with a used needle can transmit bloodborne disease such as hepatitis, AIDS and other similar diseases. As a result, there is a present need for methods and devices to enclose the used disposable needle by providing a covering for the used needle tip after it has been withdrawn from the patient.

Many needle guards are known. Certain techniques include placing a separate needle cap over the needle after use, positioning a sliding shield distally over the used needle, or hiding the withdrawn needle within a hollow needle bearing holder. Many of the current needle guards require a two-handed technique in order to activate the guard. Such a two-handed technique is awkward to use and may still pose a risk of accidental needle stick.

In addition to safety shielding devices for needles which require two-handed operation, the art has also seen the use of needle shield devices which are automatically activated and do not require one-handed or two-handed operation. However, many of these shields are difficult to fabricate, awkward to use, and require additional handling steps to actuate the device.

There exists a need for a simple, straightforward, reliable, easily fabricated needle assembly which is self-contained, capable of single-handed activation, and can be used with blood collection and intravenous delivery devices.

SUMMARY OF THE INVENTION

The present invention has been developed to overcome the disadvantages of the prior art. A needle assembly is provided which allows for safe removal and disposal of used needles without risk of exposure to bloodborne pathogens. The needle assembly allows for use of a one-handed needle removal technique.

A shielded needle assembly is provided for protection against exposure to bloodborne pathogens by protecting the sharp tip of a used needle. The needle assembly of the present invention includes a needle, a needle shield, and a flexible actuator arranged toward a proximal end of the needle and releasably connected to the shield. A resilient band is interposed between the actuator and the needle shield. The needle shield is capable of moving from a retracted position in which a tip of the needle is exposed to an extended position covering the needle and shielding the needle tip. The resilient band urges the needle shield over the needle to guard the needle tip upon actuatable release of the flexible actuator.

A needle shield assembly is provided, including an elongate needle having a proximal end and a distal needle tip. A needle shield is provided for slidable movement from a retracted position in which the needle tip is exposed to an extended position in which the needle tip is covered. A flexible actuator is fixedly positioned toward the proximal end of the needle and releasably connected to the needle shield for actuatable release thereof. A resilient band is attached to the shield urges and the shield along the needle to cover the distal tip upon release of the shield.

Additionally, a needle shield assembly is provided, including an elongate needle having a proximal end and a distal needle tip. A needle shield is provided for slidable movement from a retracted position in which the needle tip is exposed, to an extended position in which the needle tip is covered. A substantially H-shaped flexible actuator is fixedly positioned toward the proximal end of the needle and releasably connected to the needle shield for actuatable release thereof. A resilient band is attached to the shield for urging the shield along the needle to cover the distal tip.

These and other features of the invention will be better understood through a study of the following detailed description and accompanying drawings.

BRIEF DESCRIPTION OF THE DRAWINGS

FIG. 6A is a side view of the needle assembly according to FIG. 5 with the shield member in the retracted position.

DETAILED DESCRIPTION OF THE PREFERRED EMBODIMENTS

The present invention provides a needle assembly for preventing contact with the tip of a used needle by providing a needle shield which, when retracted, allows the needle tip to be exposed, but when extended, blocks access to the tip of the needle and protects against needle stick injuries.

As used herein, the top of a needle assembly is that part having the bevel of the needle. The bevel faces away from the patient's skin when the needle is inserted into a vein. The bottom of a needle assembly is 180° from the top, while the sides of the needle assembly are 90° from either the top or the bottom of the assembly.

Figure 1:
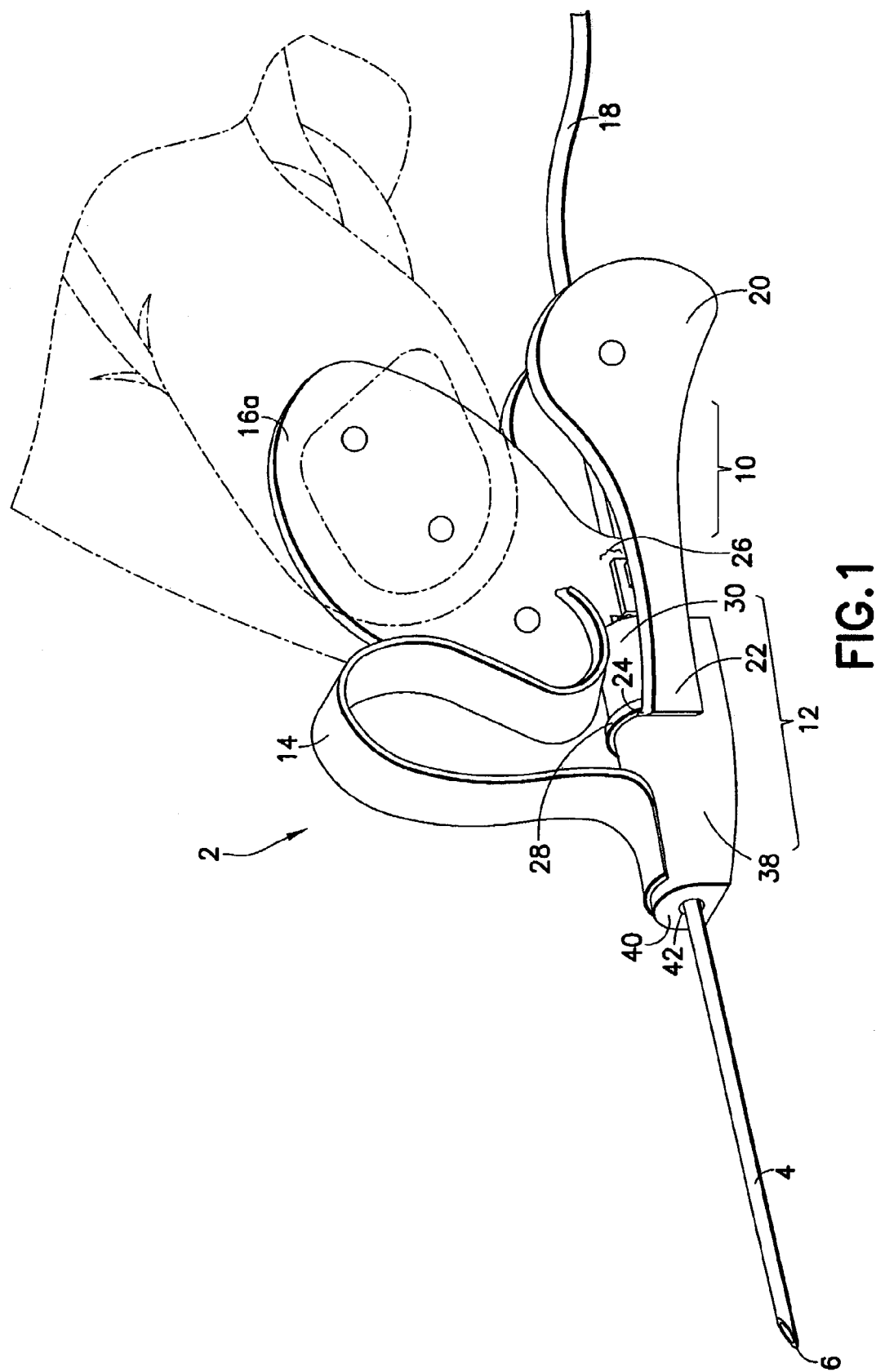
FIG. 1 is a perspective view of a needle assembly of the present invention with the shield member in the retracted position.

Referring to the drawings in which like characters refer to like members throughout the several views, FIG. 1 shows an embodiment of the needle assembly according to the present invention. The needle assembly, referred to generally by the reference numeral 2, includes a hollow needle 4. The needle 4 possesses a distal tip 6 which is used to access a patient's bloodstream. A shield member 12, also referred to as a needle shield and/or simply as the shield, is provided to protect the tip 6 of the needle 4 after it has been contaminated. Tubing 18 is in fluid communication with the needle 4 for transport of fluid to or from the patient. A flexible actuator 10 is arranged toward a proximal end of the needle shield 12. A guide member in the form of a fin 16a is provided on the actuator 10 for guiding placement of the needle 4 during venipuncture. A biasing element in the form of a resilient band 14 connects the shield 12 and the actuator 10.

The shield 12 is positioned about the needle 4 and is releasably connected to the actuator 10. The shield 12 is capable of movement from a retracted position as illustrated in FIG. 2A, in which the tip 6 of the needle 4 is exposed, to an extended position as illustrated in FIG. 2B, in which the tip 6 of the needle 4 is covered.

Figure 2A:
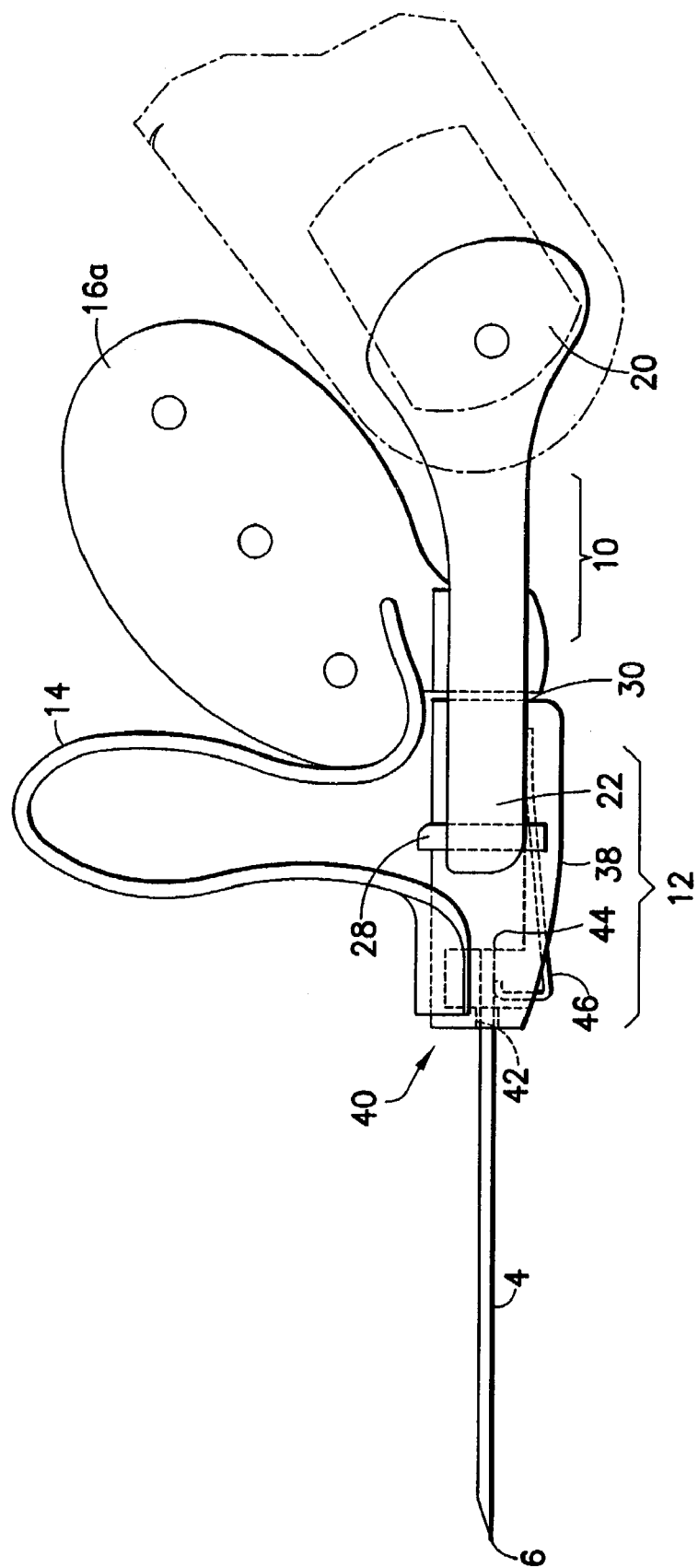
FIG. 2A is a side view of the needle assembly according to FIG. 1 with the shield member in the retracted position.
Figure 2B:
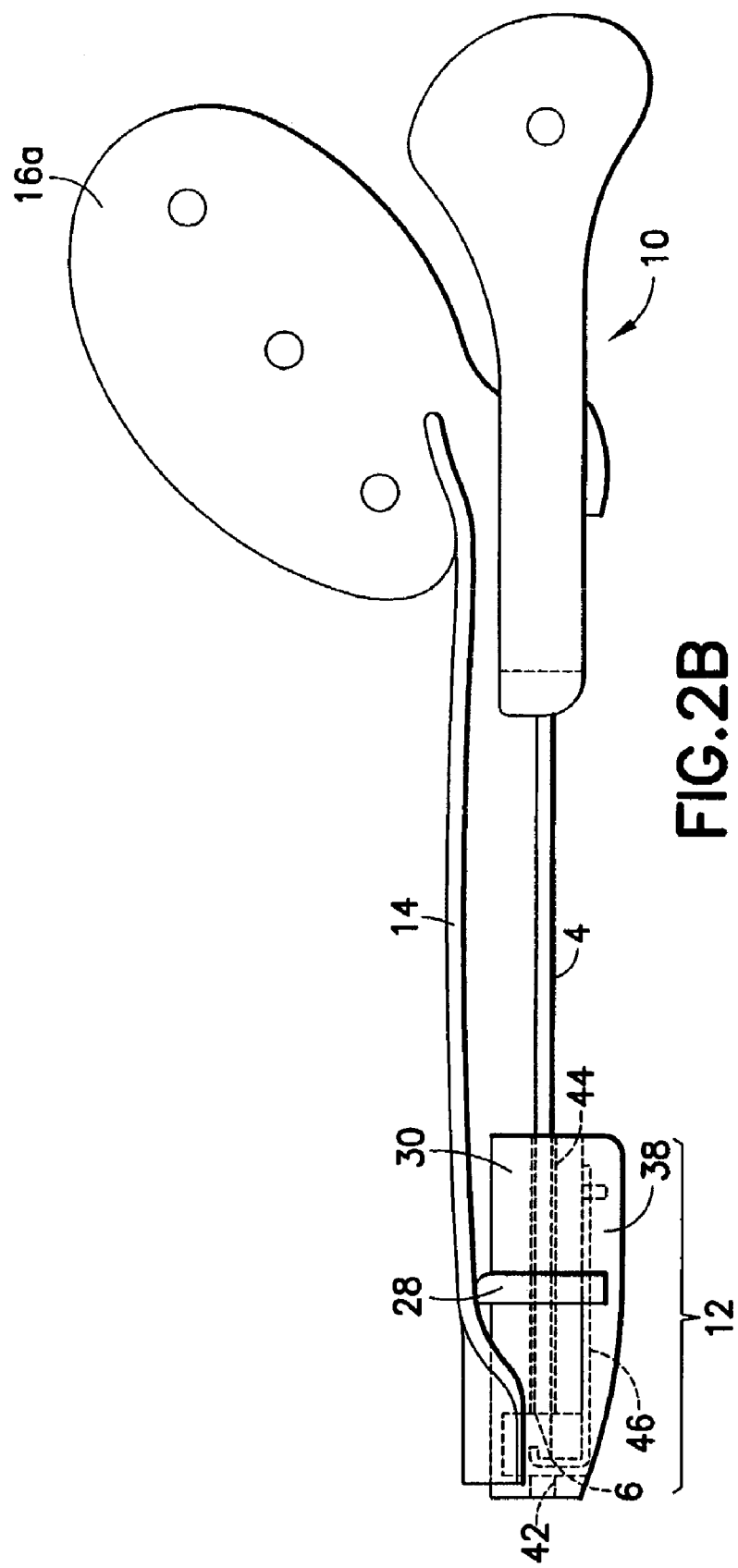
FIG. 2B is a partial side view of the needle assembly according to FIG. 1 with the shield member in the extended position.

As best seen in FIG. 2A, the shield 12 includes a proximal annular portion 30 and a distal blunting end 40 joined by an elongate barrier arm 38. The blunting end 40 has a distal aperture 42 and a proximal needle passageway 44. The needle 4 is positioned within the proximal annular portion 30 and the proximal needle passageway 44 of the blunting end 40 of the shield member 12. Any conventional shield may be used as the shield member. An appropriate shield for this purpose is disclosed, for example, in U.S. Pat. No. 5,738,665.

Referring again to FIG. 2A, when the shield 12 is in the retracted position, the tip 6 of the needle 4 passes completely through the shield 12 and is exposed through the distal aperture 42. In this position, the needle tip 6 is exposed and available for use to access a patient. As shown in FIG. 2B, when the shield 12 is in the extended position, the tip 6 of the needle 4 is withdrawn from the distal aperture 42 and is protected within the shield 12. In this position, the needle tip 6 is shielded and unintentional contact, such as a needle stick, is prevented.

Figure 7:
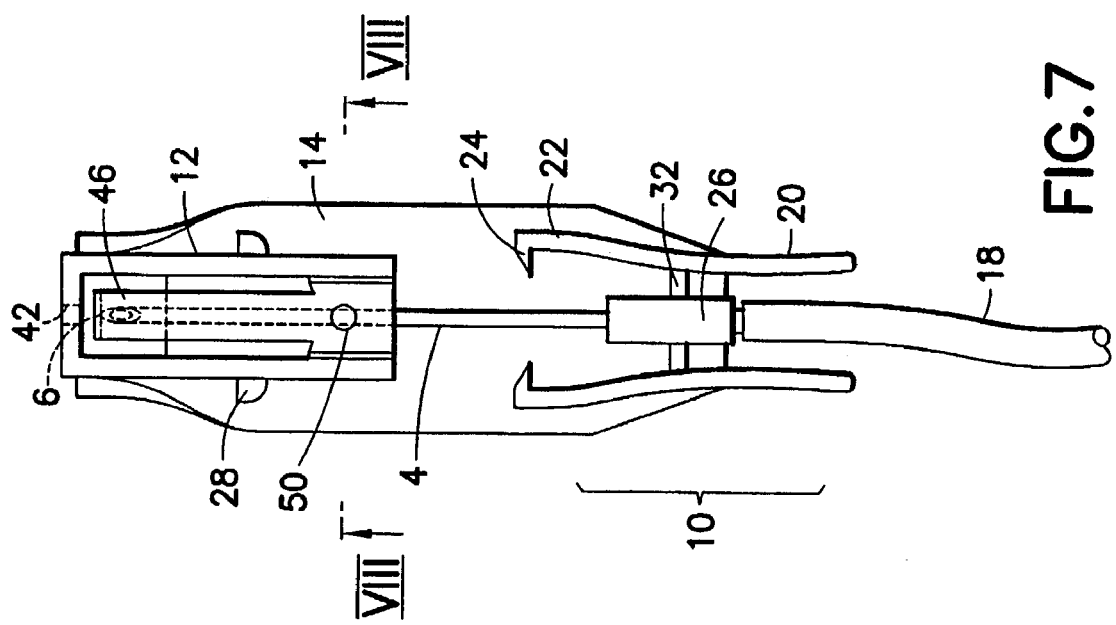
FIG. 7 is a bottom plan view of a needle assembly according to the present invention.
Figure 9:
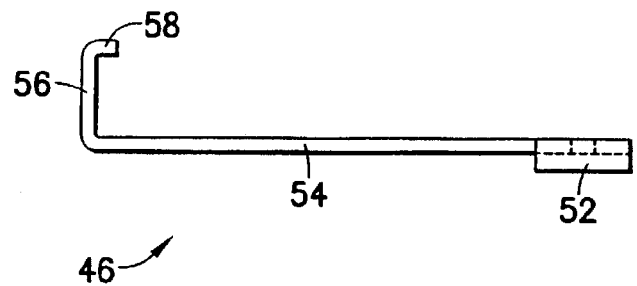
FIG. 9 is a side view of a leaf spring of the needle assembly according to the present invention.
Figure 11A:
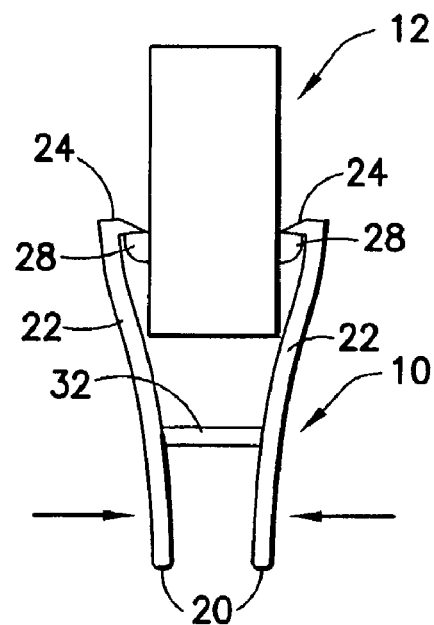
FIGS. 11A and 11B are schematic views of the mode of operation of the actuator in releasing the shield.
Figure 11B:
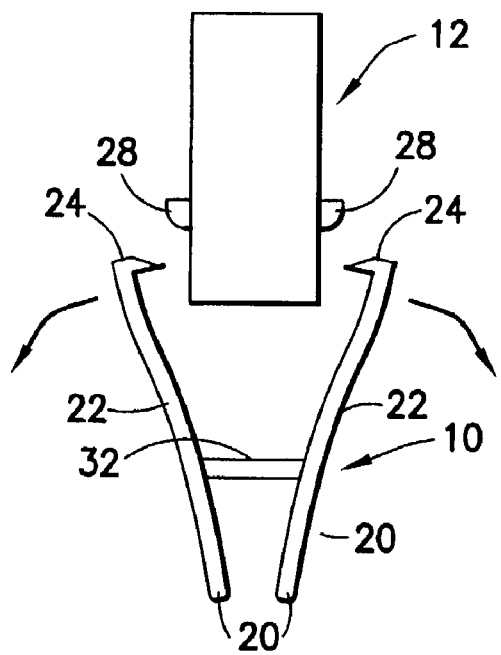

In the configuration of the invention as shown in FIGS. 7, and 11A and 11B, the actuator 10 is substantially "H"-shaped. The actuator 10 includes an actuating member 20 and a retaining member 22 with a pivot 32 therebetween. Specifically, the actuator 10 includes elongate arms. The elongate arms include proximal actuating arms 20 running laterally toward a distal end of the assembly 2 and distal latching arms 22 running laterally toward a proximal end of the assembly 2. In this embodiment, the pivot 32 includes a central tubular portion 26 which circumscribes the needle 4 toward a proximal end thereof. The central tubular portion 26 serves as a point of attachment of the actuator 10 to the needle 4. Both the latching arms 22 and the actuating arms 20 are connected to the central tubular portion 26 via the pivot 32. It is to be understood that other arrangements of attachment of the elongate arms are possible so long as the arms are capable of pivoting to actuably release the shield from the actuator.

Toward a distal end of each of the latching arms 22 is a coupling member in the form of inwardly facing hooked ends 24. The hooked ends 24 fit over oppositely directed lugs 28 on the shield member 12. When the hooked ends 24 of the latching arms 22 are fitted over the lugs 28, the shield member 12 is secured in the retracted position so that the needle tip 6 is exposed.

It is to be understood that although a pair of latching arms and lugs are shown, it is also possible to have a single latching arm. In this case, a single latching arm will possess a hooked end. The actuator arm on the side of the actuator opposite the latching arm may be relatively inflexible and serve a support function for one or more fingers. The actuating arm in linear alignment with the latching arm will be flexible so as to permit release of the actuator from the shield upon application of pressure to the flexible actuating arm. Furthermore, it is within the scope of the invention for the connection between the actuator and shield to be formed of equivalent structures, such as a protrusion of the actuator fitting into a recess on the shield, or any other equivalent structures.

The simplicity of design and operation of the actuator 10 is best seen in schematic FIGS. 11A and 11B. In FIG. 11A the actuator 10 is shown in position over lugs 28 of the shield 12. Application of pressure on the actuating arms 20 toward one another causes a pivoting motion about the pivot 32 which forces the latching arms 22 to move away from one another as shown in FIG. 11B. This movement releases the connection between the actuator 10 and the shield 12, specifically between the hooked ends 24 of the latching arms 22 and the lugs 28 of the shield 12.

The actuator is a simple integrally formed flexible member that may readily be fabricated using known molding techniques. The flexibility of the one-piece actuator is all that is required to create a reliable releasable connection with the shield member. The simplicity of design enables manufacture of a needle shield assembly in a simple and cost-efficient manner.

Figure 3:
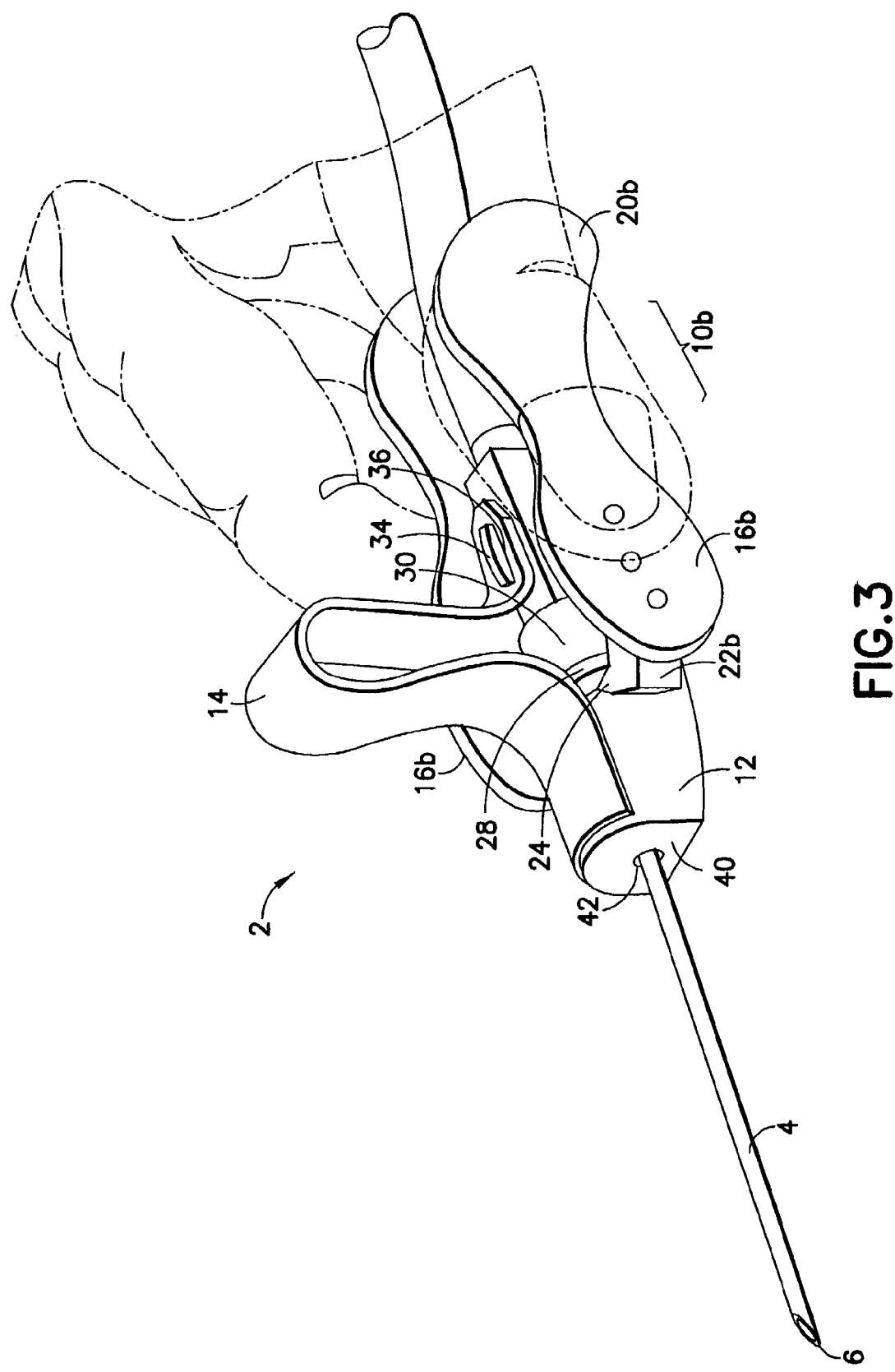
FIG. 3 is a perspective view of a needle assembly of the present invention with the shield member in the retracted position.

Referring now to FIG. 3, a biasing element in the form of a resilient band 14 is arranged on the top of the needle assembly 2. Resilient band 14 is an elongate generally planar member. A proximal end of the band 14 includes a slot 36 for attaching the band 14 to the actuator 10. The actuator 10 includes a boss 34 for this purpose. The slot 36 fits over the boss 34 to connect the resilient band 14 to the actuator 10. The distal end of the band 14 is connected to the top of the shield 12 by an adhesive or other appropriate securement member. It is to be understood that any appropriate means for attaching the band 14 to the actuator 10 and the shield 12 may be used.

When the actuator 10 is at rest, the shield 12 is maintained in the retracted position by the connection between the hooked ends 24 of the latching arms 22 of the actuator 10 and the lug 28 of the shield 10. In this retracted position, the needle tip 6 is exposed and available for use, and the resilient band 14 is arched and possesses an elastic potential energy.

There are no particular limitations to the material with which the resilient band 14 is made so long as the band resists memory deformation in the arched shape that it assumes when the shield 12 is retracted. Thus, suitable materials include any elastomeric or flexible material which does not maintain shape memory. One particularly suitable material is a silicone band. Others will be readily apparent to one having skill in the art.

Upon application of digital pressure to the elongate actuating arms 20, the latching arms 22 are moved outwardly, away from the needle 4, releasing the connection between the shield member 12 and the actuator 10. This motion actuates conversion of the potential energy stored in the resilient band 14 to kinetic energy. The kinetic energy of the released band 14 moves the shield member 10 distally along the needle 4 until the blunting end 40 of the shield 12 covers the needle tip 6.

The guide member may take a variety of different forms. Referring again to FIG. 3, an alternative configuration of the guide member is shown. In this aspect, a portion of the actuator 10b may additionally serve the function of the guide member. Here, the latching arms 22 of the actuator 10b includes contact surfaces such as finger pads 16b which serve the function of the guide member. In this embodiment, a user may safely apply pressure to the actuator 10b at this point and avoid releasing the connection between the actuator 10b and the shield member 12. Specifically, application of a pressure at this location will further press the latching arms 22 toward one another, thus reinforcing the connection between the actuator 10b and the shield member 12.

Figure 4A:
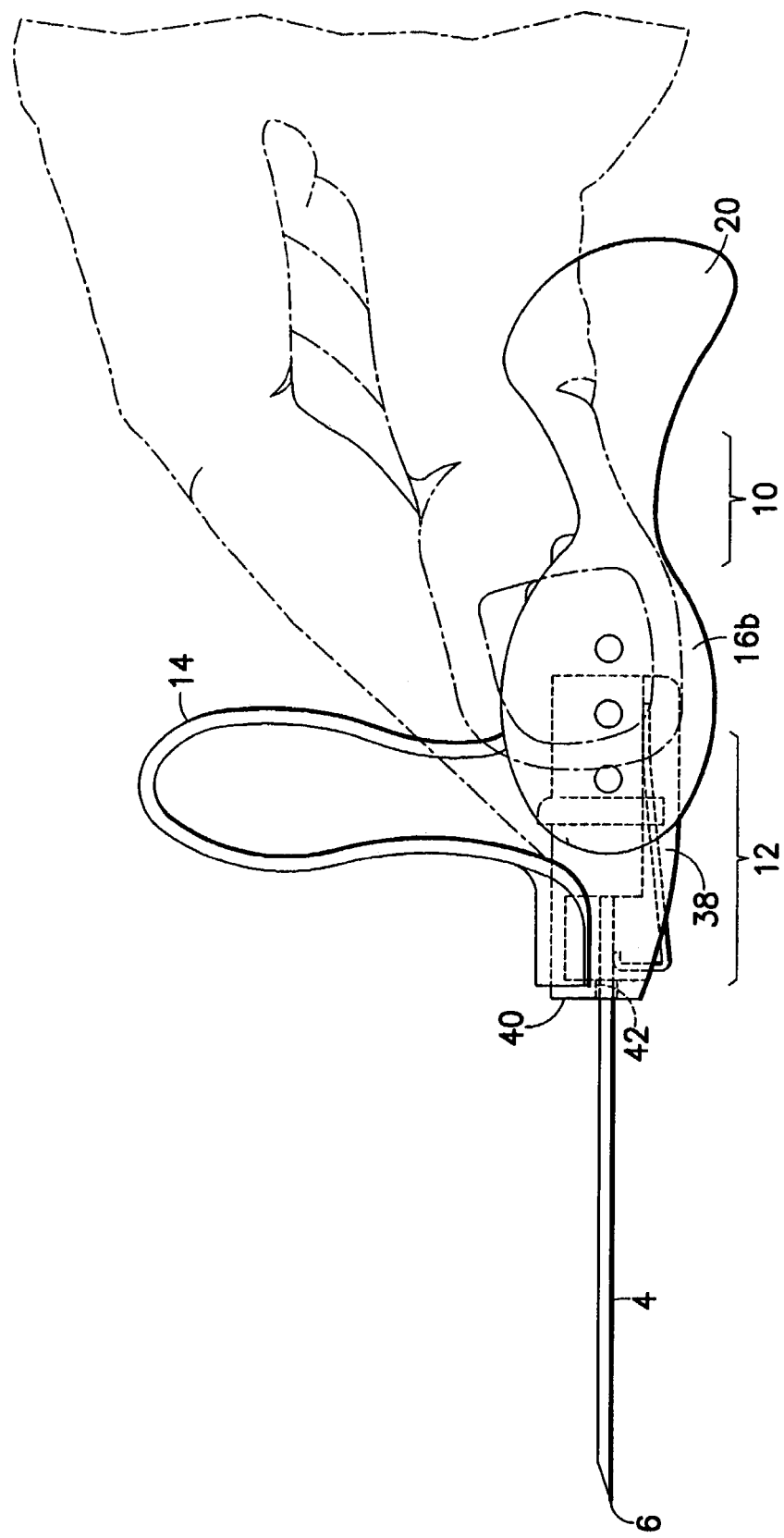
FIG. 4A is a side view of the needle assembly according to FIG. 3 with the shield member in the retracted position.

The position of a user's hand to guide a needle into a patient in this embodiment is best shown in FIG. 4A. In operation, a user will hold the latching arms 12 of the actuator 10 at the finger pads 16b while guiding the needle 4 into a patient.

Figure 4B:
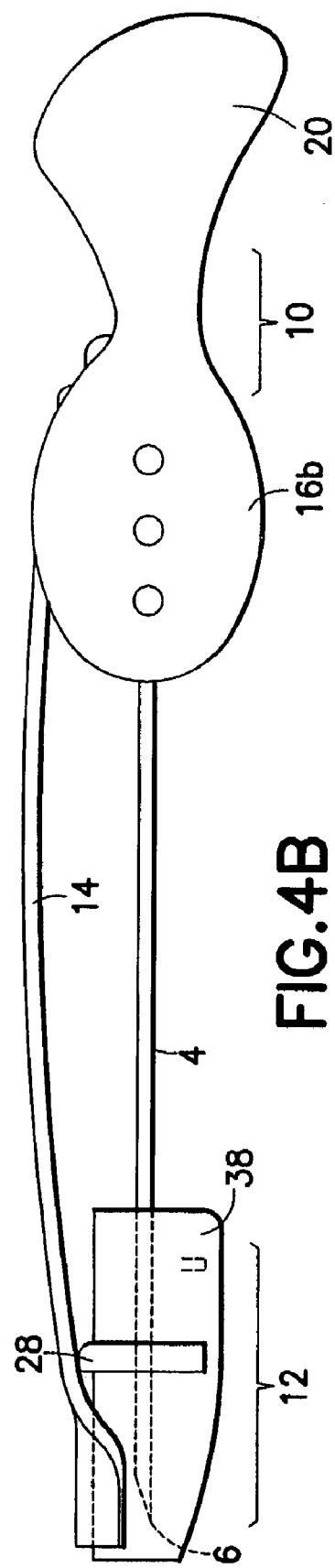
FIG. 4B is a partial side view of the needle assembly according to FIG. 3 with the shield member in the extended position.

In this embodiment, when the needle is to be withdrawn, the user may hold the actuating arms 20b of the actuator 10b to withdraw the needle. In this case, the user may apply a further pressure to the actuating arms 20. Upon application of the further pressure, the actuator 10 will force the hooked ends (not shown) out of position over the lug (not shown), releasing the connection between the actuator 10 and the shield 12, and allowing the elastic potential energy of the resilient band 14 to be released. The resilient band 14 will then move the shield 12 over the needle tip 6 as shown in FIG. 4B.

Alternatively, the user may hold the actuating arms 20 of the actuator 10 to withdraw the needle while simultaneously applying sufficient pressure to the actuating arms 20 so as to release the connection between the actuator 10 and the shield member 12. In this case, the shield 12 abuts the skin of the patient while the needle 4 is being withdrawn. Once the needle 4 is entirely withdrawn from the patient, the kinetic energy of the released resilient band 14 will move the shield 12 over the tip 6 of the needle 4. The band 14 will then be extended in a linear fashion as opposed to being arched, and will have forced the shield member 12 over the needle tip 6.

Figure 5:
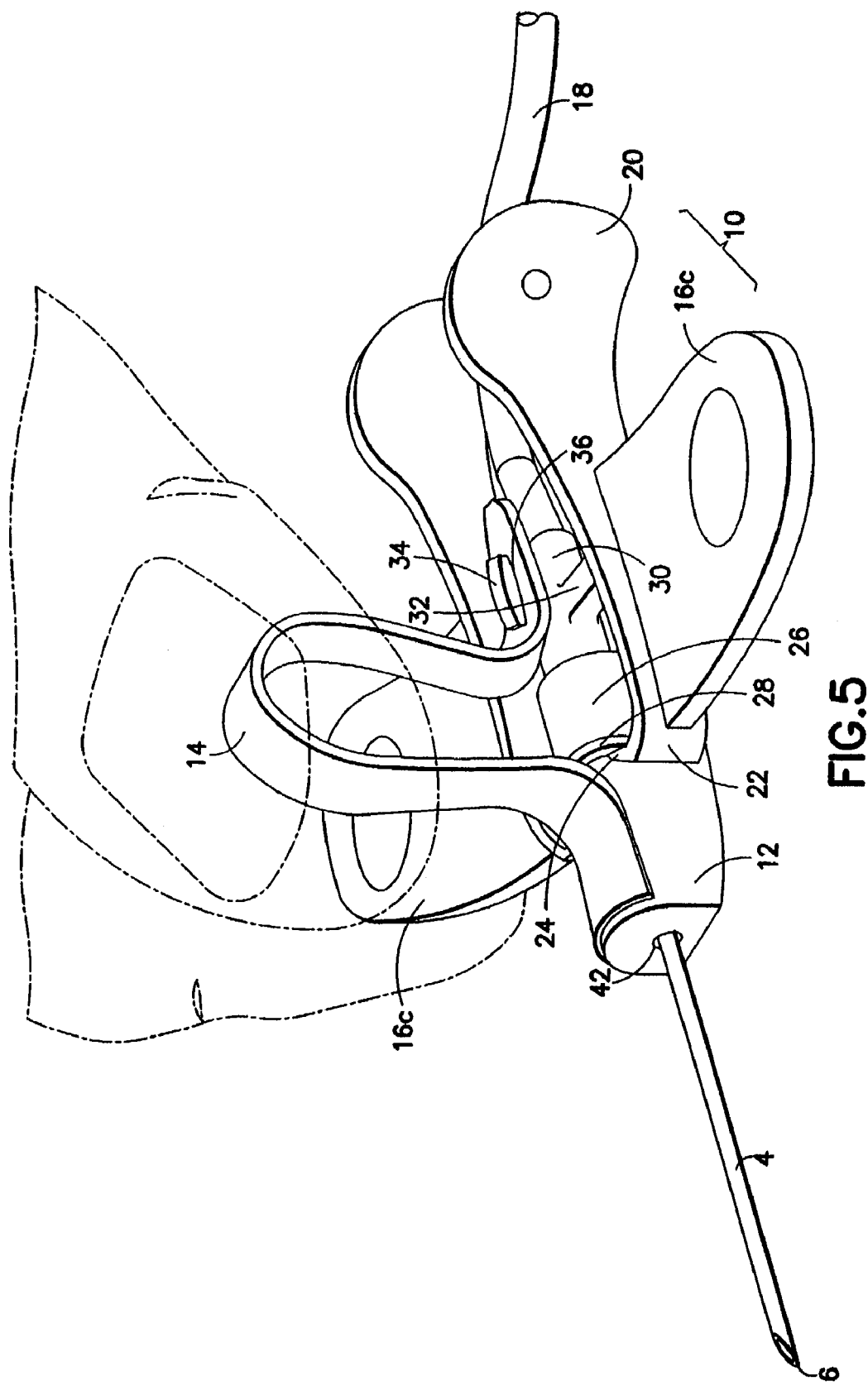
FIG. 5 is a perspective view of an alternative embodiment of the needle assembly of the invention with the shield member in the retracted position.

Another alternative embodiment of the present invention is shown in FIG. 5. In this aspect, the guide member is in the form of two laterally placed opposed wings 16c. In this case, the wings 16c are formed integrally with the latching arms 22 of the actuator 10. A user may hold the wings 16c together at the top of the needle assembly 2 when inserting the needle 4 into a patient.

Referring now to FIGS. 5 and 6A, possible positions of a user's hand when removing the needle 4 from a patient are shown. In FIG. 5, the user holds a wing 16c to remove the needle 4. In FIG. 6A, the user holds the actuating arms 20 to remove the needle 4. In this case, the actuator 10 may be actuated before, during, or after removal of the needle 4 by timing the further application of pressure to activate the actuator 10.

Each of the various embodiments of guide members may be formed integrally with the actuator, or may be formed separately from the actuator, and then attached, for example, by an adhesive, thermobonding or other suitable means.

Once a needle assembly according to the present invention has been used, and the shield member has been positioned over the needle tip, it is important to maintain the position of the shield member over the needle tip. It is therefore desirable to prevent retrograde motion of the shield to prevent re-exposure to the used needle and any resultant needle stick injuries this would entail. Thus, in a further embodiment of the invention, a locking member is provided.

Figure 8:
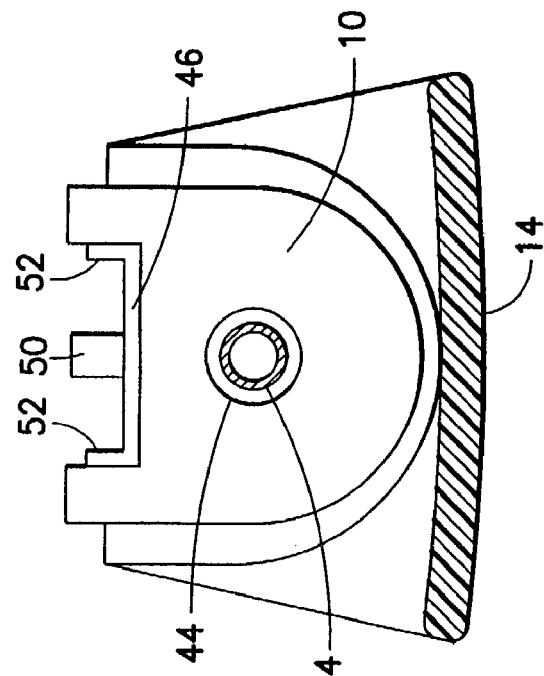
FIG. 8 is a cross sectional view of the needle assembly according to FIG. 7 along the VIII—VIII line shown in FIG. 7.

Referring now to FIGS. 6A, 9, 10A and 10B, a locking member according to the invention is shown. The locking member is a tensioned leaf spring 46 shown positioned toward a bottom of the shield 12. The leaf spring 46 has a relatively flat rectilinear surface 54 including an orifice 52 for fastening the leaf spring 46 to the shield 12. A boss 50 toward the proximal end of the shield 12 fits into the orifice and fastens the leaf spring 46 to the shield 12. In FIG. 8, which is a cross sectional view along line VIII—VIII of FIG. 7, the leaf spring 46 is shown having a pair of tabs 52 angled at an approximately 90° angle from the rectilinear surface 54 for further securement of the leaf spring 46 to the shield 12. The distal end of the leaf spring 46 is bent upward substantially perpendicular to the rectilinear surface 54 and defines a cover plate 56 for covering the needle tip 6. The cover plate 56 further includes a flange 58 which assists in maintaining the cover plate 56 in position over the needle tip 6.

Figure 10A:
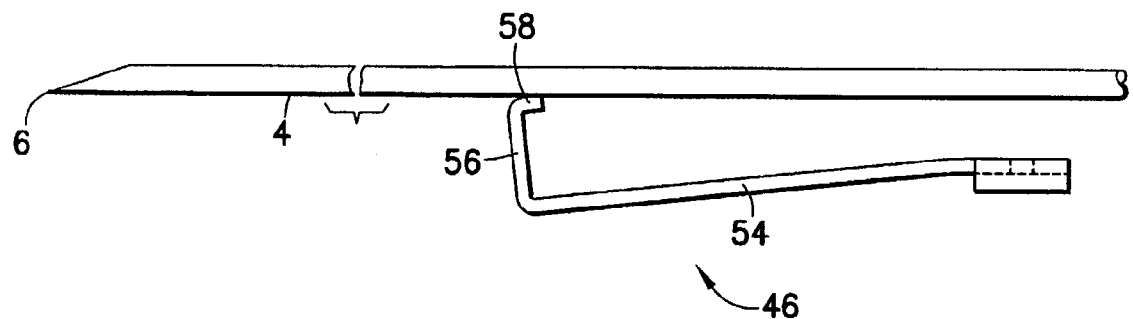
FIG. 10A is a side view of the leaf spring of FIG. 9 bearing against the needle.
Figure 10B:
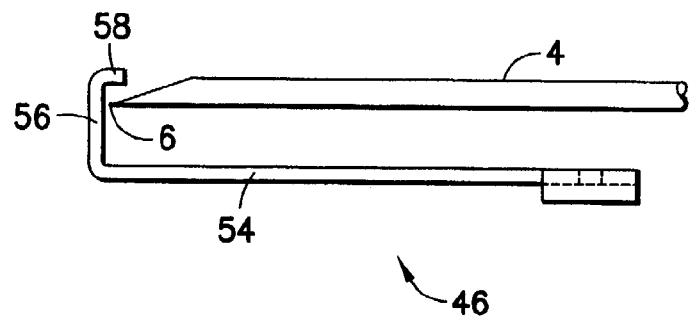
FIG. 10B is a side view of the leaf spring of FIG. 9 covering the tip of the needle.

As best shown in FIG. 10A, the leaf spring 46 is designed to bear against the shaft of the needle 4 when the shield 12 is retracted. As shown in FIG. 10B, the leaf spring 46 covers tip 6 of the needle 6 of the shield 12 when the shield is in the extended position.

Figure 6B:
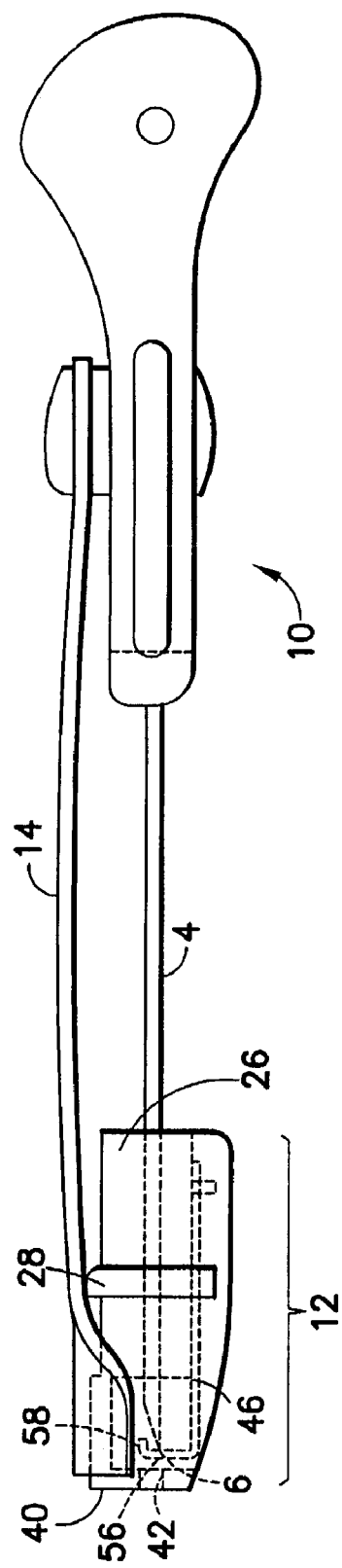
FIG. 6B is a partial side view of the needle assembly according to FIG. 5 with the shield member in the extended position.

The mode of operation of the leaf spring 46 is shown in FIGS. 10A and 10B. When the shield 12 is in the retracted position, as in FIG. 10A, the leaf spring 46 bears against the shaft of the needle 4 with a certain amount of tension. When the shield 12 is released, the resilient band 14 moves the shield 12 including the leaf spring 46 along the shaft of the needle 4 until the leaf spring 46 reaches the tip 6 of the needle 4. At this point, the tension on the leaf spring 46 provided by the needle 4 is released. This released tension moves the cover plate 56 in place over the tip 6 of the needle 4. This is best shown in FIGS. 10B and 6B. In this position, the distal aperture 42 of the blunting end 40 of the shield 12 is covered by the cover plate 56 and the needle tip 6 is effectively prevented from movement through the aperture 42. In this way, the leaf spring 46 prevents retrograde movement of the shield 12 back over the needle 4.

Preferably, the needle assembly of the invention is used with blood collection devices. Generally, two types of blood collection devices are employed. In one type of blood collection device, illustrated infra, blood is drawn into a flexible tubing prior to collection in a blood collection tube. In another type of blood collection device, blood is drawn directly from the collection needle into a blood collection tube. Each of these blood collection devices usually includes a hollow, cylindrical tubular body (the needle holder) in fluid communication with either a single-ended or double-ended needle at the point of collection of the blood sample. The holder serves, inter alia, to provide protection against exposure to blood splatter and/or glass which may occur as a result of collection tubes breaking or malfunctioning during blood collection. It is to be understood that the needle assembly of the present invention may be used with any blood collection device for providing protection from exposure to used needles.

When blood is drawn directly into a blood collection tube, a double-ended needle is used. In this case, a proximal end of the needle extends into the needle holder and is covered with a flexible sleeve. A distal end of the needle extends outwardly from the needle holder for insertion into a patient's vein. In this arrangement, the holder is arranged proximate to the blood collection needle. See, for example, U.S. Pat. No. 5,687,740, the entirety of which is herein incorporated by reference.

Blood collection devices as discussed above, draw blood from a patient using evacuated tubes, such as those sold under the trade name VACUTAINER (Becton Dickinson). Evacuated tubes have a closed end and an open end with a closure therein and are used in conjunction with a needle holder assembly. The vacuum in the tubes assists in drawing blood from a patient's blood stream.

When used in combination with evacuated tube blood collection systems wherein blood is drawn directly into blood collection tubes, the structure of the needle shield assembly is substantially similar to the assembly illustrated in FIGS. 1–11A and B. Accordingly, substantially similar components that perform substantially similar functions are numbered identically to those components of the embodiment of FIGS. 1–10A and 10B except that a suffix is used to identify alternative embodiments of the components in FIGS. 12 to 19.

Figure 12:
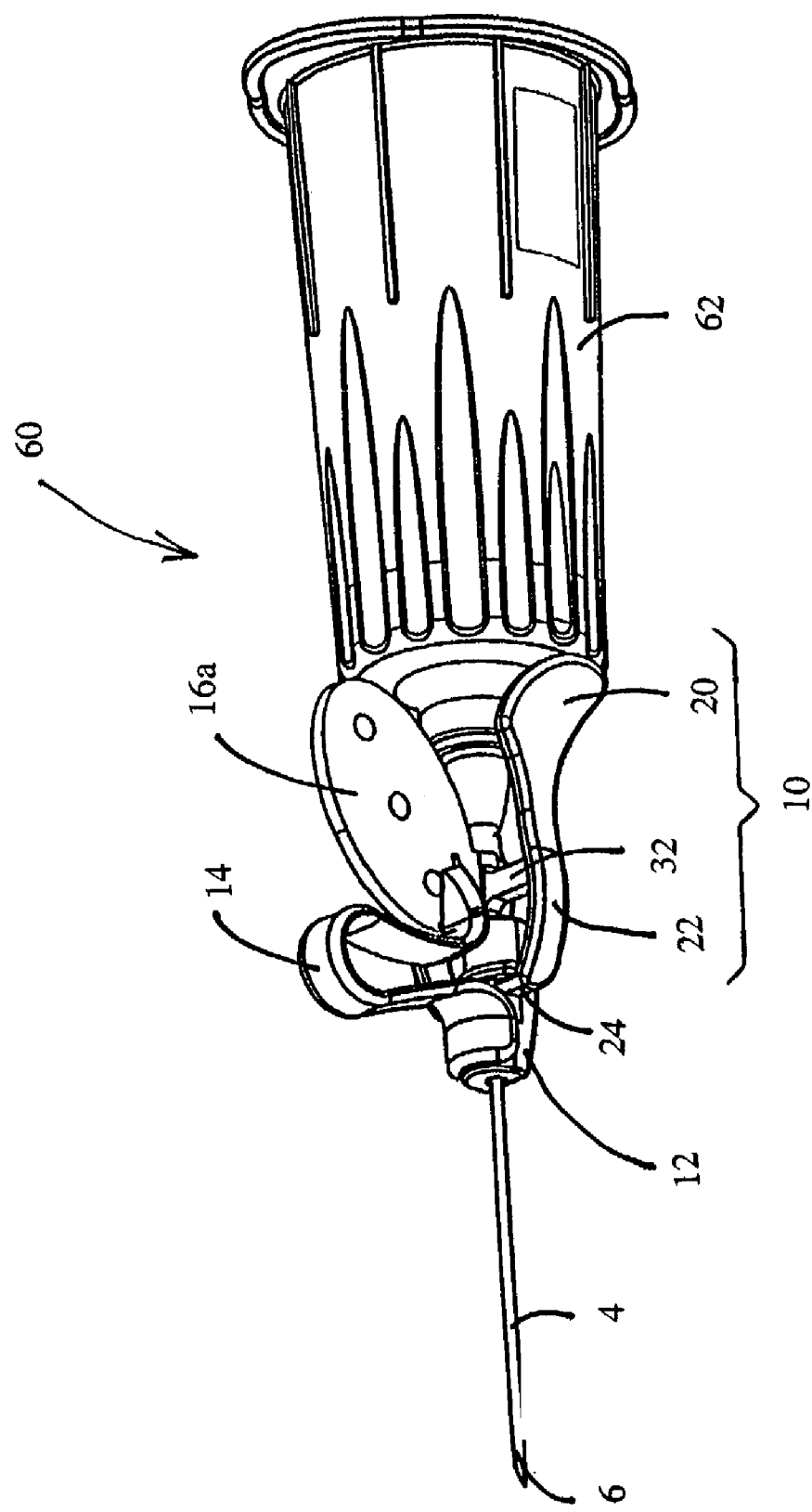
FIG. 12 is a perspective view of an embodiment of the invention shown with an evacuated tube blood drawing system.
Figure 13:
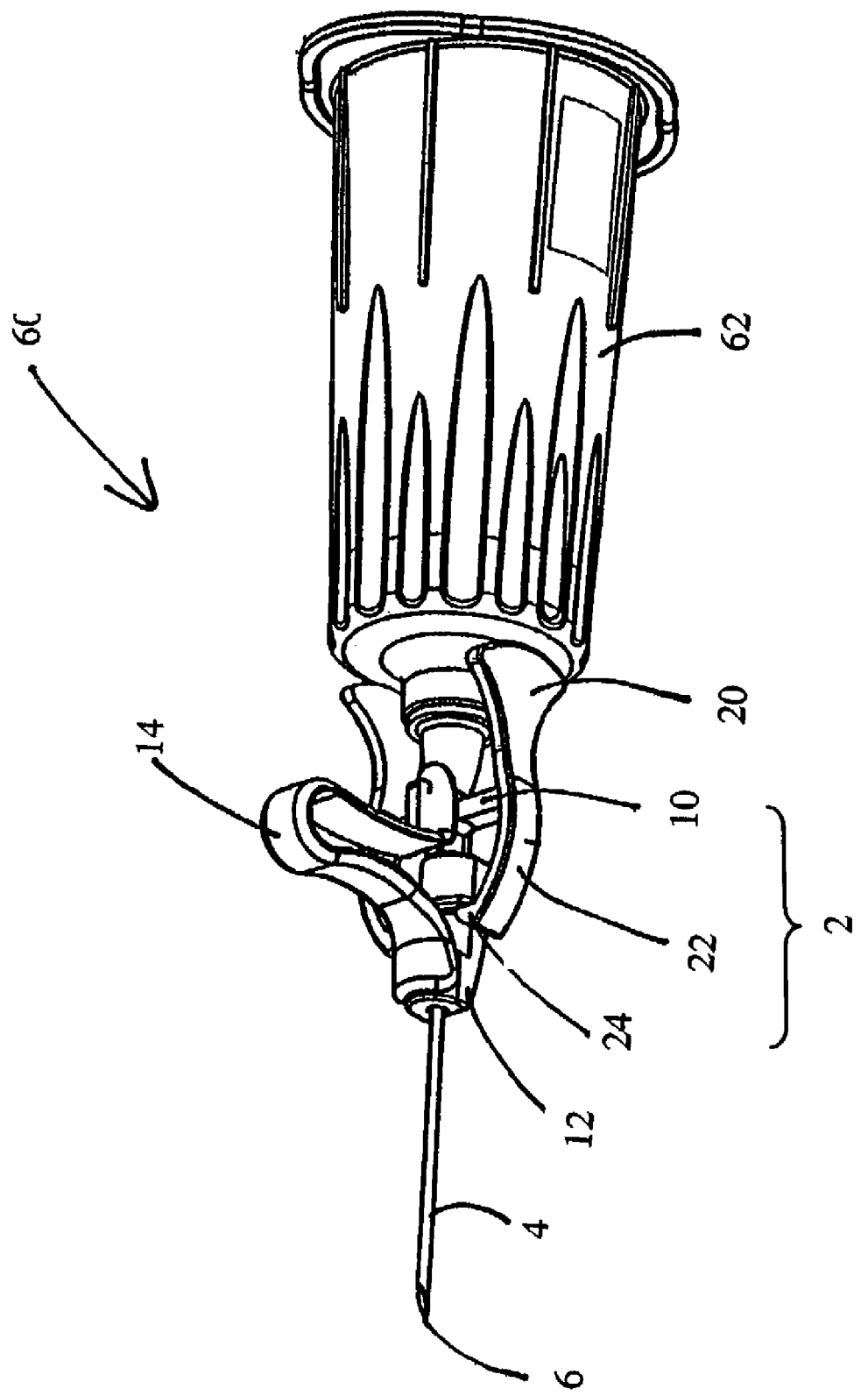
FIG. 13 is a perspective view of an embodiment the invention shown with an evacuated tube blood drawing system.

Referring now to FIGS. 12 and 13, a needle shield according to the present invention is shown as part of a blood collection system as described above, in which the needle is attached directly to a holder in an assembly 60. In FIG. 12, the needle shield assembly including an actuator 10 with a guide member in the form of a fin 16a, is shown with the shield 12 in the retracted position. The operation of the needle assembly is essentially as described previously. In this embodiment, the pivot 32 may be made to have a more elongate construction so as to provide necessary clearance between the actuating arms 20 and the distal end of the needle holder 62.

In FIG. 13, a needle shield assembly 2 with the needle shield 12 in the retracted position is shown including an actuator 10 having an exterior portion of the latching arms 22 serving as the guide member. The operation of the shield assembly 2 is essentially as described previously. In this embodiment, the pivot 32 may be constructed as in FIG. 12, with elongate members providing sufficient clearance between the actuating arms and the distal end of the needle holder 62.

Figure 14:
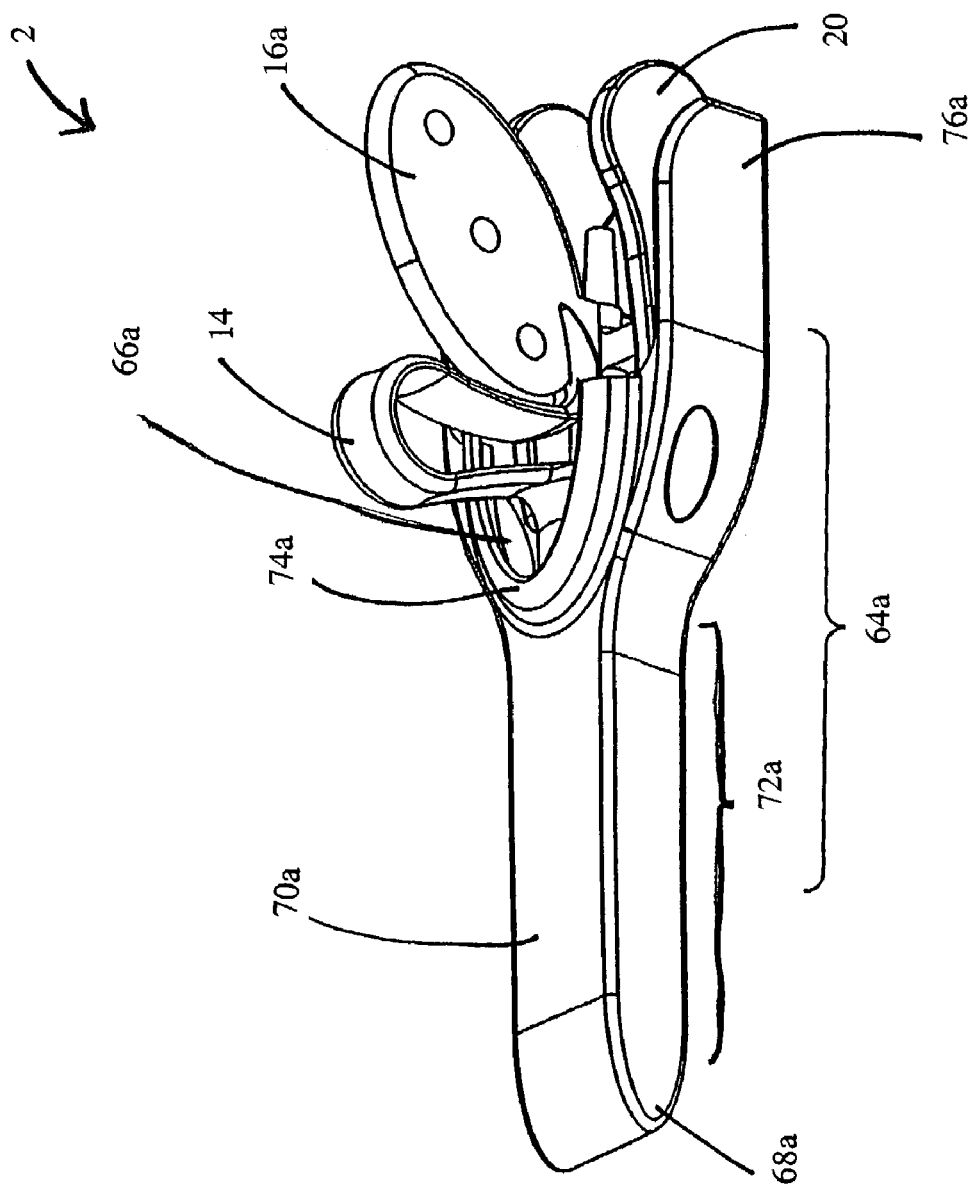
FIG. 14 is a perspective view of an embodiment of the needle assembly of the invention including an safety cap useful for the needle assemblies shown in FIGS. 1 and 12.

The needle assembly may further include a securement member for protection of the needle before use. The securement member also serves to protect the user from the needle tip prior to use. Additionally, the securement member secures the connection between the shield and actuator, preventing inadvertent premature activation of the actuator during shipping and handling prior to use. Referring now to FIG. 14, a securement member in the form of a safety cap 64a is shown for use with the embodiments of the invention described in FIGS. 1 and 12 in which the needle assembly 2 includes a fin guide member 16a. The cap 64a is an elongate member with an open proximal end 66a, a distal end 68a and a polygonal sidewall 70a which defines the shape of the cap 64a. Distal end 68a is preferably closed. The cap 64a includes a distal portion 72a which covers and protects the needle tip (not shown). A cut out portion 74 on the top of the cap 64a is shaped to accommodate the resilient band 14. The open proximal end 66 of the cap 64a includes two elongate members 76a running laterally along the sides of the needle assembly 2. Specifically, the elongate members 76a at least partially overlap and cover the actuating arms 20.

Figure 15:
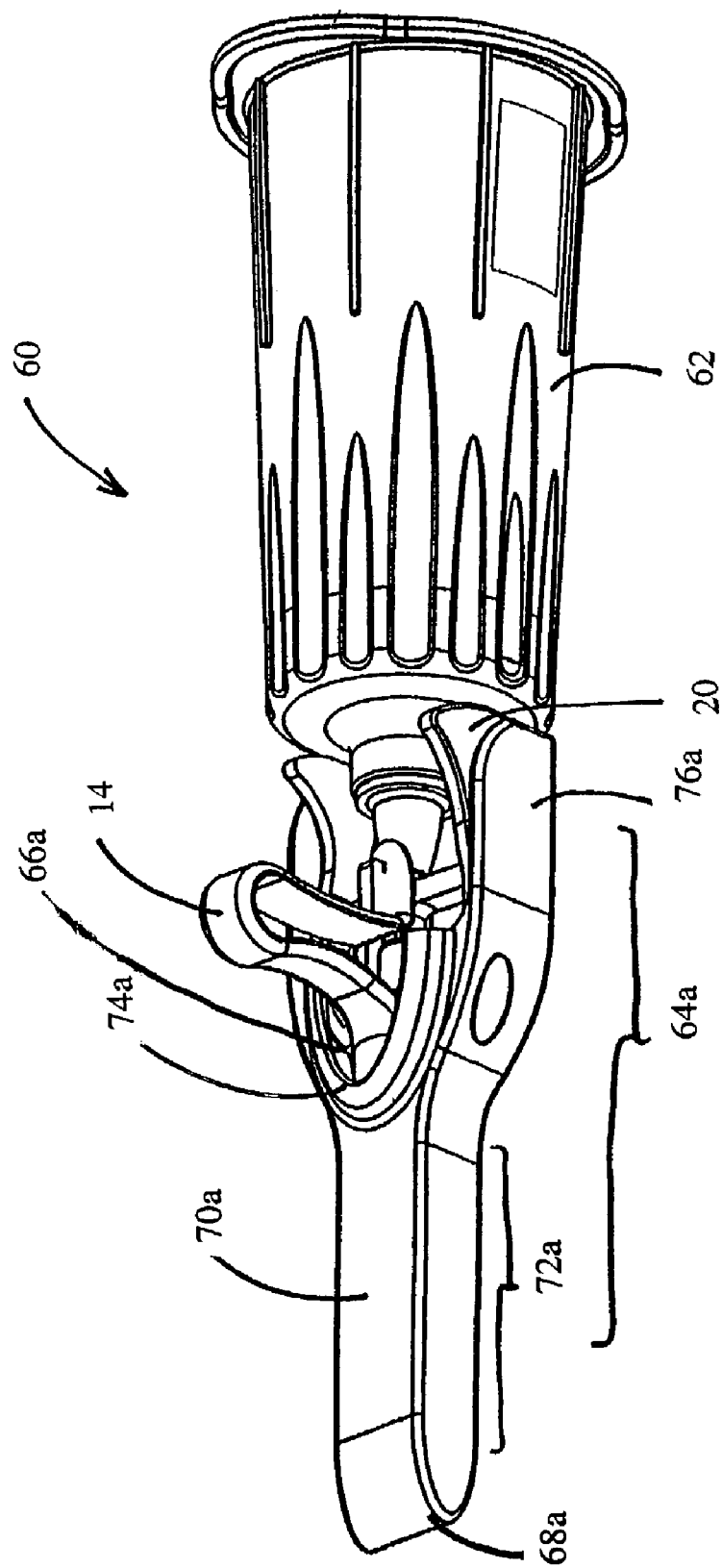
FIG. 15 is a perspective view of an embodiment of the needle assembly of the invention including a safety cap useful for the needle assemblies shown in FIGS. 3 and 13.

Referring now to FIG. 15, the safety cap 64a of FIG. 14 is shown for use with the embodiment of the invention shown in FIG. 13. As in the previous embodiment, the cap 64a is an elongate member with an open proximal end 66a, a distal end 68a and a sidewall 70a which defines the shape of the cap 64a. Distal end 68a is again, preferably closed. The cap 64a includes a distal portion 72a which covers and protects the needle tip (not shown). A top cut out portion 74a on the top of the cap 64a is shaped to accommodate the resilient band 14. The open proximal end 66a of the cap 64a includes two elongate members 76a running laterally along the sides of the needle assembly 2. Specifically, the elongate members 76a at least partially overlap and cover the actuating arms 20 of the actuator 10. The finger pad guide member (not shown) is secured inside the cap 64a.

Figure 16:
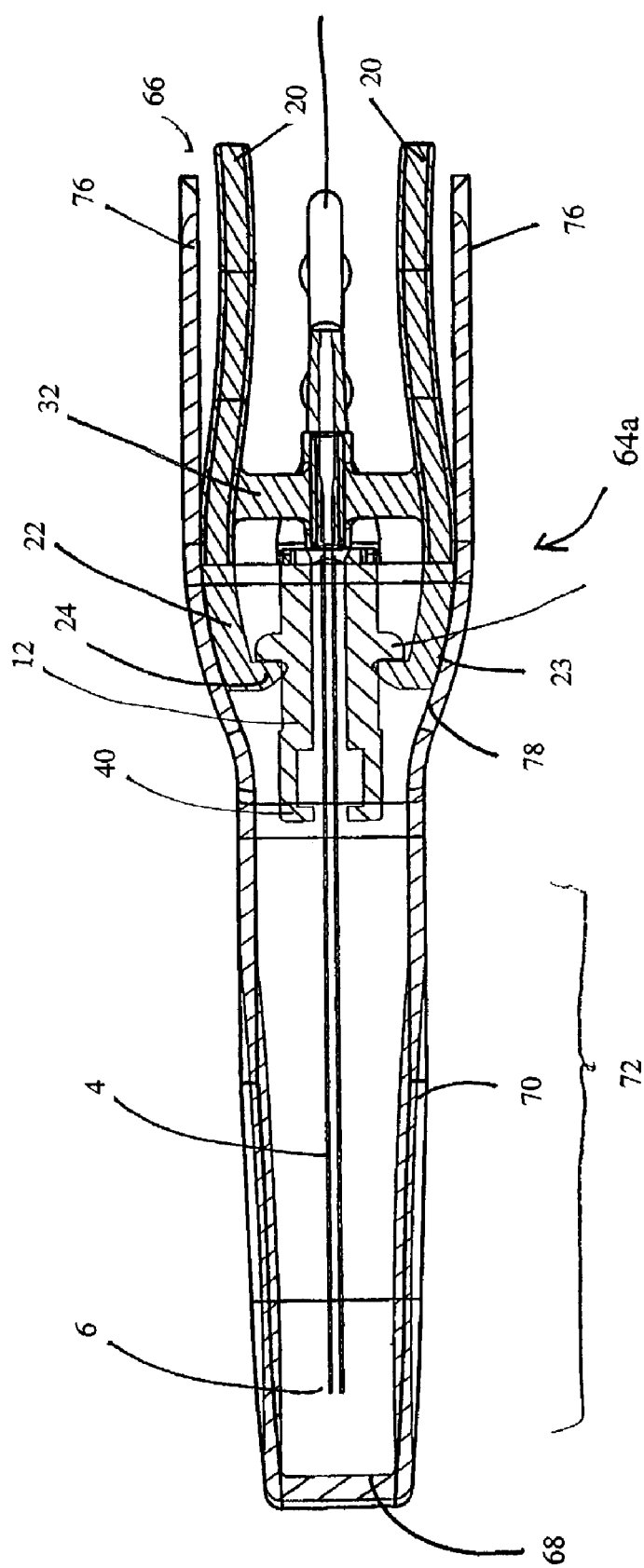
FIG. 16 is a cross sectional top view of the safety cap shown in FIGS. 14 and 15.

Referring now to FIG. 16, a top cross sectional view of the cap according to FIG. 15 is shown. An exterior surface 23 of latching arms 22 is shown in abutting contact with a portion of an interior surface 78 of the safety cap 64a. In this configuration, it is clear that the pivot 32 is prevented from performing its function when the cap 64a is in place on the assembly 2. Even upon application of a pressure to the actuator arms 20, the hooked ends 24 of the latching arms 22 will still maintain a connection with the lugs 28 of the shield 12.

Figure 17:
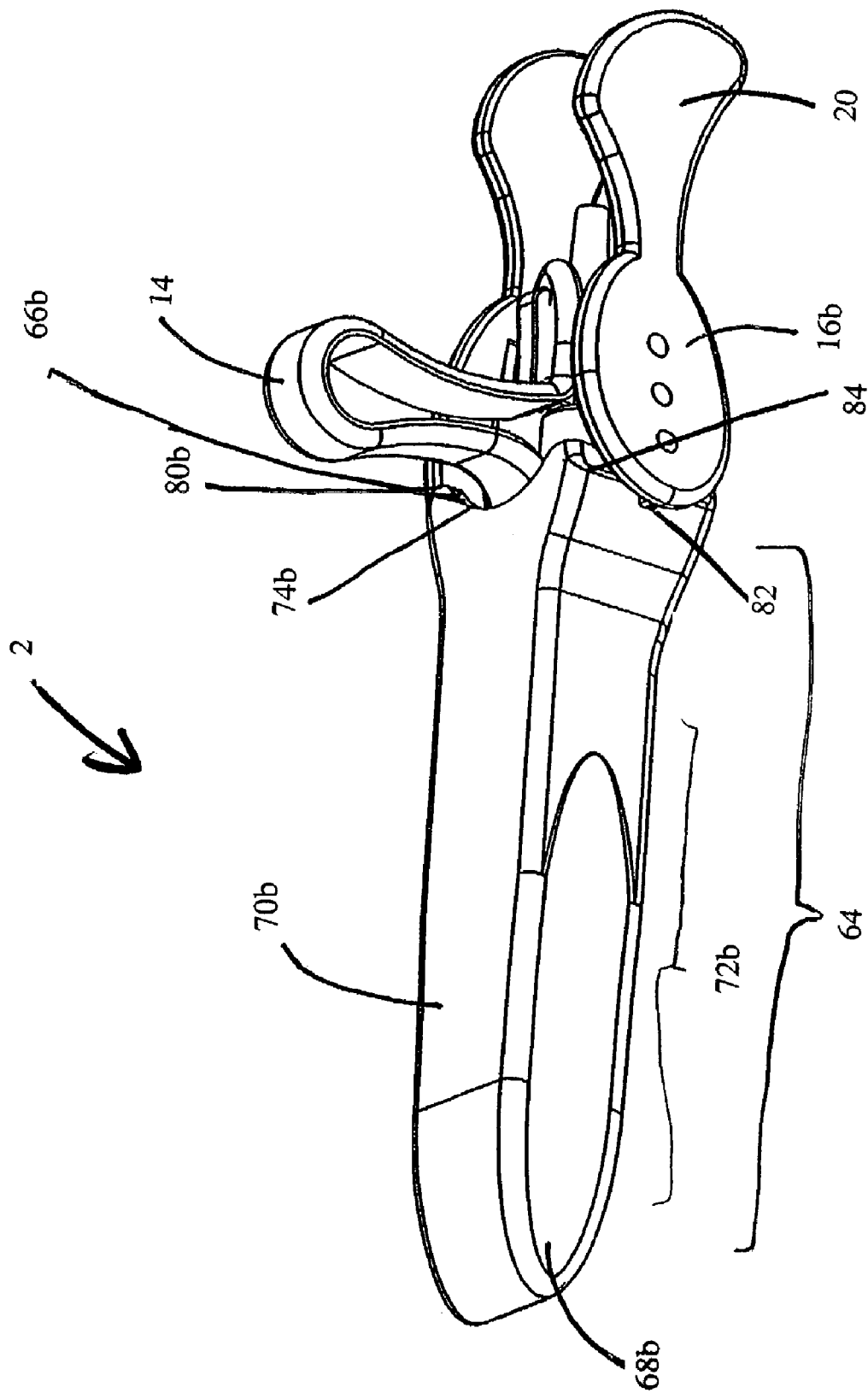
FIG. 17 is a perspective view of an alternative embodiment of a safety cap useful for the needle assemblies shown in FIGS. 3 and 13.
Figure 18:
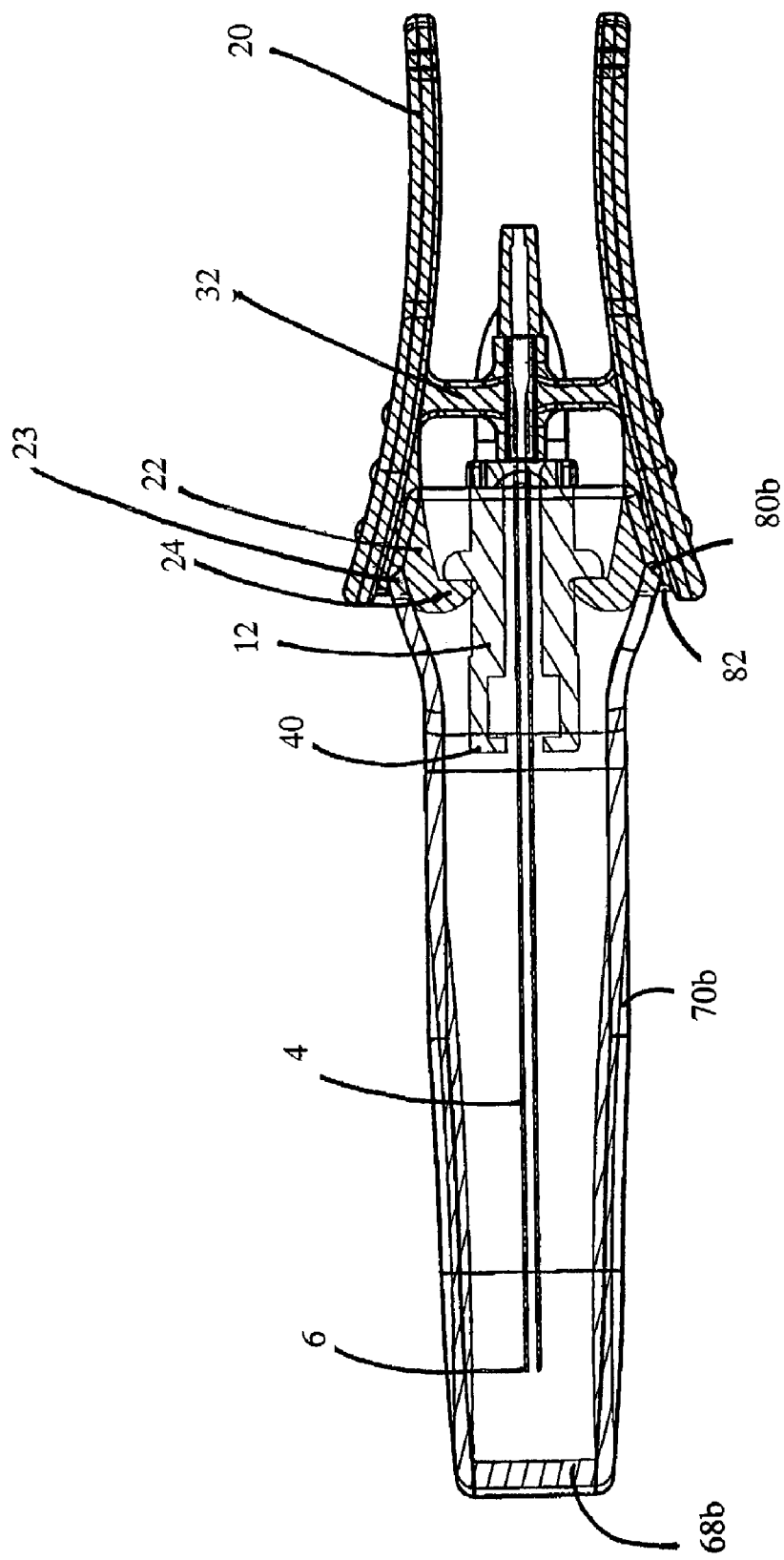
FIG. 18 is a cross sectional top view of the safety cap shown in FIG. 17.

Referring now to FIGS. 17 and 18, an alternative safety cap 64b for use with an assembly having contact pad guide members 16b is shown. In this configuration, the cap 64b is as described previously, with an elongate member having an open proximal end 66b, a distal end 68b and a polygonal sidewall 70b which defines the shape of the cap 64b. Distal end 68b is again, preferably closed. The cap 64b includes a distal portion 72b which covers and protects the needle tip (not shown). A top cut out portion 74*b* on the top of the cap 64*b* is shaped to accommodate the resilient band 14. Additionally, the open proximal end 66*b* of the cap 64*b* ends in a substantially blunt edge 80*b* sized to fit between a distal portion of the finger pads 16*b* and an exterior surface 23 of the latching arms 22. The cap 64*b* is shown with a raised rib 84 toward the blunt edge 80*b* of the cap 64*b*.

The cap may merely end at the blunt edge or it may include a raised rib to engage a coupling member on the finger pads. As shown in FIGS. 17 and 18, the finger pads 16*b* include a coupling member 82 to further secure the connection between the cap 64*b* and the assembly 2. The coupling member 82 fits over and engages the raised rib 84 of the cap 64*b* in a snap fit arrangement when the cap 64*b* is in place on the assembly 2. In this configuration, the finger pad guide member 16*b* remains outside the cap 64*b* while the latching arms 22 are covered by the cap 64*b*. It is also possible for other snap fit configurations known in the art to be used. For example, the coupling member may snap fit into a corresponding indent or orifice in the cap.

Figure 19:
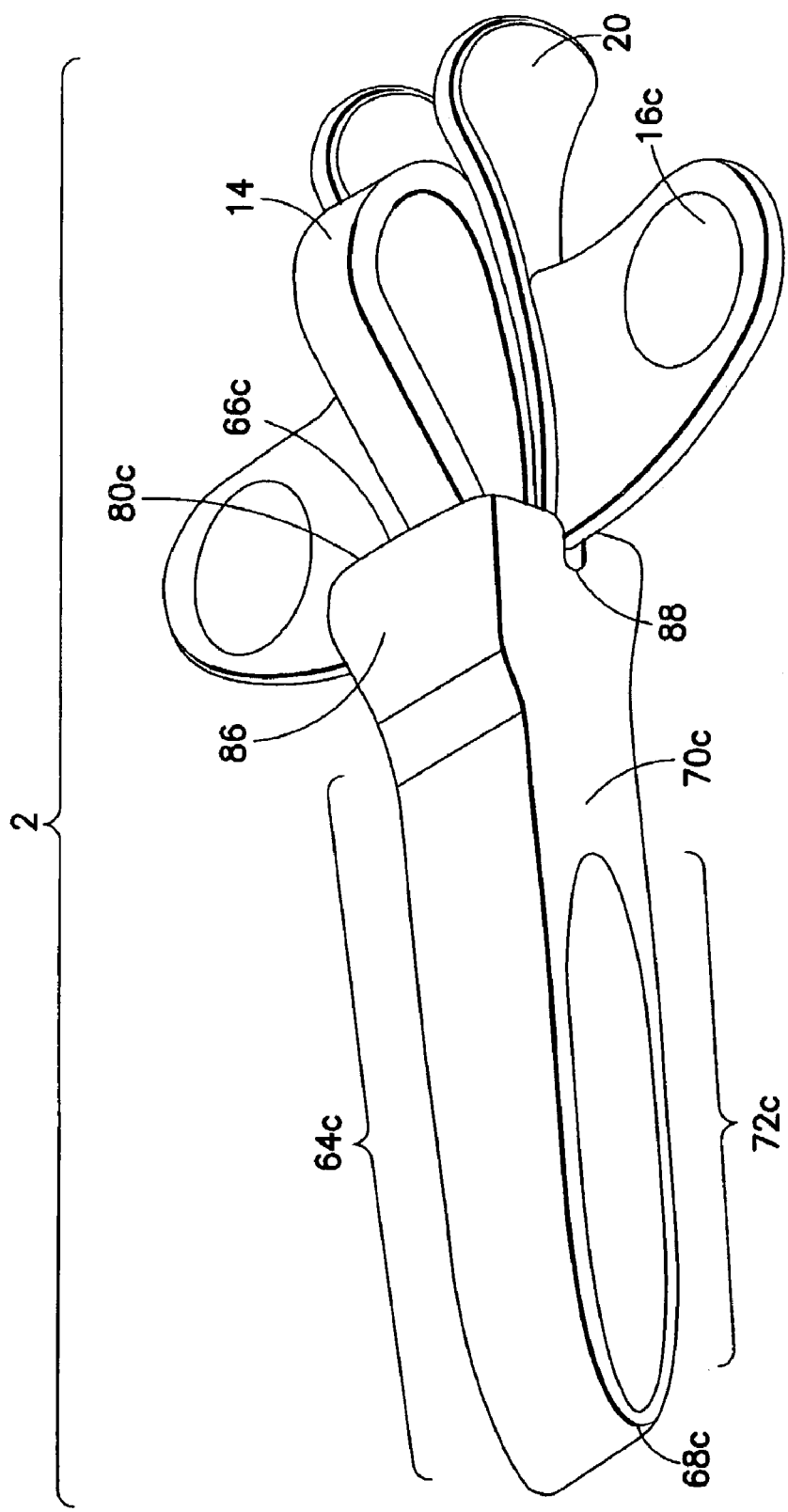
FIG. 19 is a perspective view of an embodiment of the needle assembly of the invention including a safety cap useful for the needle assembly shown in FIG. 5.

Referring now to FIG. 19, an alternative safety cap 64*c* for use with an assembly having winged guide members 16*c* is shown. In this configuration, the cap 64*c* is as described previously, with an elongate member having an open proximal end 66*c*, a distal end 68*c* and a polygonal sidewall 70*c* which defines the shape of the cap 64*c*. Distal end 68*c* is again, preferably closed. The cap 64*c* includes a distal portion 72*c* which covers and protects the needle tip (not shown). In contrast to the previously described embodiments, the cap includes a raised portion 86 to fit over a distal portion of the resilient band 14. The open proximal end 66*c* of the cap 64*c* ends in a substantially blunt edge 80*c* including side cut out portions 88 for accommodating a distal portion of the wings 16*c*. When in place over the needle assembly 2, the safety cap 64*c* is secured to the assembly by a friction or snap fit with at least an exterior surface of the latching arms (not shown). The cap 64*c* effectively stops inadvertent release of the connection between the actuator 10 and the shield 12 by preventing the pivot 32 from moving the latching arms 22 away from the shield 12.

In each of the aforementioned embodiments, the cap of the invention is connected to the needle shield assembly by a friction fit between an inside surface of the cap and at least a portion of an exterior surface of the latching arms of the actuator. The cap may be removed from the assembly by simply holding the assembly at a point other than the actuator arms, for example by the guide member and the cap. The cap may then be removed by pulling the cap distally away from the assembly.

Performance of the cap in preventing inadvertent activation of the actuator is twofold. First, access to the actuator arms is limited by the elongate members which provide a barrier from contact with the actuator. Second, the inside of the cap is in close enough relation with the exterior of the latching arms so as to secure the connection of the latching arms with the shield. Therefore, even if access to the actuator arms is possible, the actuator will not be activated because the cap provides a physical barrier to release of the connection between the latching arms and the shield.

Suitable materials for forming the cap and shield of the invention include, but are not limited to, thermoplastic polymeric resins such as polypropylene, polystyrene, polycarbonate, acrylonitrile/butadiene/styrene, and the like. In a preferred embodiment, the cap is a rigid member formed of molded thermoplastic. The needle is traditionally made of stainless steel, although other metals and alloys are feasible.

The needle assembly according to the invention may be used in conjunction with any conventional blood collection device or may be adapted to any specimen collection device which requires protection from the fluid being collected. Additionally, the present invention may be used in conjunction with intravenous delivery systems which pose a similar hazard of exposure to both bloodborne diseases as well as contact with the substance being delivered.

Although illustrative embodiments of the present invention have been described herein with reference to the accompanying drawings, it is to be understood that the present disclosure is to be considered as exemplary of the principles of the invention and is not intended to be limited to those precise embodiments, and that various other changes and modifications may be effected therein by one skilled in the art without departing from the scope or spirit of the invention.

What is claimed is:

1. A shielded needle assembly, comprising:
    an elongate needle having a proximal end and a distal needle tip;
    a needle shield for slidable movement from a refracted position in which said distal needle tip is exposed to an extended position in which said needle tip is covered;
    a flexible actuator fixedly positioned toward said proximal end of said needle and releasably connected to said needle shield for actuatable release thereof,
 wherein said actuator comprises a pair of opposed elongate arms having a pivot therebetween, said elongate arms having proximal ends and distal ends, whereby upon application of a pressure urging said proximal ends toward each other, said distal ends move away from each other, thereby releasing said shield; and
    a resilient band attached to said shield for urging said shield along said needle to cover said distal tip upon said actuatable release of said shield.

2. The needle assembly according to claim 1, wherein said actuator is manually actuatable to release said needle shield.

3. The needle assembly according to claim 1, wherein a portion of said actuator is fixedly positioned about said proximal end of said needle.

4. The needle assembly according to claim 1, wherein a portion of said actuator is fixedly positioned proximal to said shield.

5. The needle assembly according to claim 1, wherein said actuator includes a central tubular portion, said central tubular portion being fixedly positioned about said proximal end of said needle.

6. The needle assembly according to claim 5, wherein said shield includes an annular portion, said annular portion being in abutting contact with said central tubular portion.

7. The needle assembly according to claim 2, wherein said shield member includes at least one lug and said actuator includes at least one flexible latching arm for releasably engaging said lug.

8. The needle assembly according to claim 7, wherein said latching arm engages said lug at a location distal to said pivot and substantially parallel to said needle.

9. The needle assembly according to claim 8, wherein said latching arm includes a hooked end facing said needle for engaging said lug.

10. The needle assembly according to claim 2, wherein said actuator is substantially H-shaped.

11. The needle assembly according to claim 10, wherein said shield includes two substantially opposed lugs and whereby said distal curls of said elongate arms are configured so as to engage said lugs.

12. The needle assembly according to claim 11, wherein said distal ends of said elongate arms further include substantially opposed hooked ends for engaging said lugs.

13. The needle assembly according to claim 1, wherein said actuator is formed of an clastomeric material.

14. The needle assembly according to claim 1, wherein said resilient band is formed of en elastomeric material without shape memory.

15. The needle assembly according to claim 13, wherein said resilient band is formed of silicone.

16. The needle assembly according to claim 1, further comprising at least one guide member for guiding placement of said needle.

17. The needle assembly according to claim 16, wherein said guide member is a pair of flexible wings.

18. The needle assembly according to claim 16, wherein said guide member is a dorsal fin.

19. The needle assembly according to claim 16, wherein said guide member is a contact surface on a portion of said actuator.

20. The needle assembly according to claim 19, wherein said contact surface is integral with said actuator.

21. The needle assembly according to claim 20, wherein said contact surface is configured so as to reinforce a connection between said actuator and said shield upon application of a digital pressure thereto.

22. The needle assembly according to claim 16, wherein said resilient band is attached to at least one of said actuator and said guide member.

23. The needle assembly according to claim 1, further comprising a locking member connected to said shield for preventing retrograde movement of said needle when said shield is in said extended position.

24. The needle assembly according to claim 23, wherein said locking member includes a leaf spring, said leaf spring being configured so as to bear against said needle when said shield is in said retracted position and to cover said tip of said needle when said shield is in said extended position.

25. The needle assembly according to claim 1, further comprising a blood collection device.

26. The needle assembly according to claim 25, wherein said blood collection device delivers blood to one of a flexible tubing and a blood collection tube.

27. The needle assembly according to claim 1, further comprising a removable securement member for covering said needle, said securement member being configured so as to cover said needle tip and to form a friction fit connection with said needle assembly.

28. The needle assembly according to claim 27, wherein said securement member is a safety cap.

29. The needle assembly according to claim 28, wherein said safety cap is configured so as to retain a connection between said actuator and said shield when said safety cap is placed over said needle.

30. The needle assembly according to claim 29, wherein an inside surface of said safety cap is adjacent to an exterior surface of said latching arm.

31. The needle assembly according to claim 30, wherein said inside surface is in abutting contact with said exterior surface.

32. A needle shield assembly, comprising:
an elongate needle having a proximal end and a distal needle tip;
a needle shield for slidable movement from a retracted position in which said needle tip is exposed, to an extended position in which said needle tip is covered;
a substantially H-shaped flexible actuator fixedly positioned toward said proximal end of said needle and releasably connected to said needle shield for actuatable release thereof,
wherein said actuator includes a pair of opposed elongate arms having proximal ends and distal ends, said elongate arms having a pivot therebetween, said actuator being configured so as to release said shield upon application of a pressure urging said proximal ends together; and
a resilient band attached to said shield for urging said shield along said needle and over said distal tip upon said actuatable release of said shield.

33. The assembly according to claim 32, wherein a portion of said actuator is fixedly positioned proximal to said shield.

34. The assembly according to claim 32, wherein said shield member includes two substantially opposed lugs, and said distal ends of said elongate arms further include substantially opposed hooked ends for engaging said lugs.

35. The assembly according to claim 32, wherein said resilient band is configured to possess a potential energy when said shield is in said retracted position and a kinetic energy when a connection between said shield and said actuator is released, said kinetic energy being sufficient to move said shield into said extended position.

36. The assembly according to claim 32, wherein said resilient band is attached to at least one of said actuator and said guide member.

37. The assembly according to claim 32, further comprising a removable securement member for covering said needle tip, said securement member being configured so as to secure a connection between said actuator and said shield.

38. The assembly according to claim 32, further comprising a blood collection device.

39. The needle assembly according to claim 38, wherein said blood collection device delivers blood to one of a flexible tubing and a blood collection tube.

* * * * *